United States Patent [19]

Van der Knaap

[11] Patent Number: Plant 6,241

[45] Date of Patent: Aug. 2, 1988

[54] CHRYSANTHEMUM PLANT NAMED BIJOUX

[75] Inventor: Jacques C. M. Van der Knaap, De Lier, Netherlands

[73] Assignee: Fides, Handelskwekerij, De Lier, Netherlands

[21] Appl. No.: 820,781

[22] Filed: Jan. 22, 1986

[51] Int. Cl.[4] ..... A01H 5/00

[52] U.S. Cl. ..... Plt./76

[58] Field of Search ..... Plt./74–79

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Bijoux particularly characterized by its soft pink tubular ray floret color; nine week response; spider/anemone capitulum form and excellent flower production.

1 Drawing Sheet

The present invention comprises a new and distinct cultivar of Chrysanthemum, botanically known as *Dendranthema morifolium,* Ramat., previously *Chrysanthemum morifolium,* Ramat., and referred to by the cultivar name Bijoux.

Bijoux is a product of a planned breeding program which had the objective of creating new Chrysanthemum cultivars with spider/anemone capitulum, pink ray floret color, 9 week response, and the ability to produce commercially acceptable quality in year around cut mum programs. Such traits in combination were not present or needed improvement in previously available commercial cultivars.

Bijoux was originated from a hybridization made in a controlled breeding program in De Lier, The Netherlands in 1980. The female parent was a first generation hybrid obtained by crossing Smile×Birkevang. The male parent of Bijoux was a first generation hybrid obtained by crossing Sapphire×Dark Flamenco. Bijoux was discovered and selected as one flowering plant within the progeny of the stated cross by Jacques C. M. Van der Knaap in July of 1981, in a controlled environment in De Lier, The Netherlands.

The first act of asexual reproduction of Bijoux was accomplished when vegetative cuttings were taken from the initial selection on Aug. 20, 1981 in a controlled environment in De Lier, The Netherlands by a technician working under formulations established and supervised by Jacques C. M. Van der Knaap. Horticultural examination of selected units initiated in April of 1982 has demonstrated that the combination of characteristics as herein disclosed for Bijoux are firmly fixed and are retained through successive generations of asexual reproduction.

Bijoux has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generlly used in commercial greenhouse practice.

The following traits have been repeatedly observed and are determined to be basic characteristics of Bijoux which, in combination, distinguish this Chrysanthemum as a new and distinct cultivar:

1. Spider/anemone capitulum form.
2. Soft pink tubular ray floret color.
3. Nine week response.
4. Excellent flower production per stem.

5. 60 mm diameter across face of capitulum.

The accompanying photographic drawing shows typical inflorescence and foliage characteristics of Bijoux with colors being as nearly true as reasonably possible in photographs of this type.

In the following description, color references are made to The Royal Horticultural Society Colour Chart. The color values were determined in April of 1982 under natural day light at De Lier, The Netherlands.

Classification:

*Botanical.*—*Dendranthema morifolium,* Ramat., cv Bijoux.

*Commercial.*—Spider/Anemone spray.

INFLORESCENCE

A. Capitulum
- *Form.*—Flat.
- *Type.*—Spider/anemone.
- *Diameter across face.*—60 mm.

B. Corolla of ray florets
- *Color (general tonality from a distance of three meters).*—Pink with yellow-pink center.
- *Color (upper surface).*—RHS 75D (both tubes and spoons).
- *Color (under surface).*—RHS 75C.

C. Corolla of disc florets
- *Color (mature).*—RHS 74D on outer periphery of discs; approximately 10A-C on inner discs with tinge of 154A.
- *Color (immature).*—RHS 154A.

D. Reproductive organs
- *Androecium.*—Only rudimentary in disc florets.
- *Gynoecium.*—Present in both disc and ray florets.

PLANT

A. General appearance:
- *Height.*—80 cm.

B. Foliage
- *Color (upper surface).*—RHS 147B.
- *Color (under surface).*—RHS 147A.
- *Shape.*—Medium to long lobed and finely serrated.

I claim:

1. A new and distinct Chrysanthemum plant named Bijoux, as described and illustrated, and particularly characterized by its soft pink tubular ray floret color; nine week response; spider/anemone capitulum form and excellent flower production.

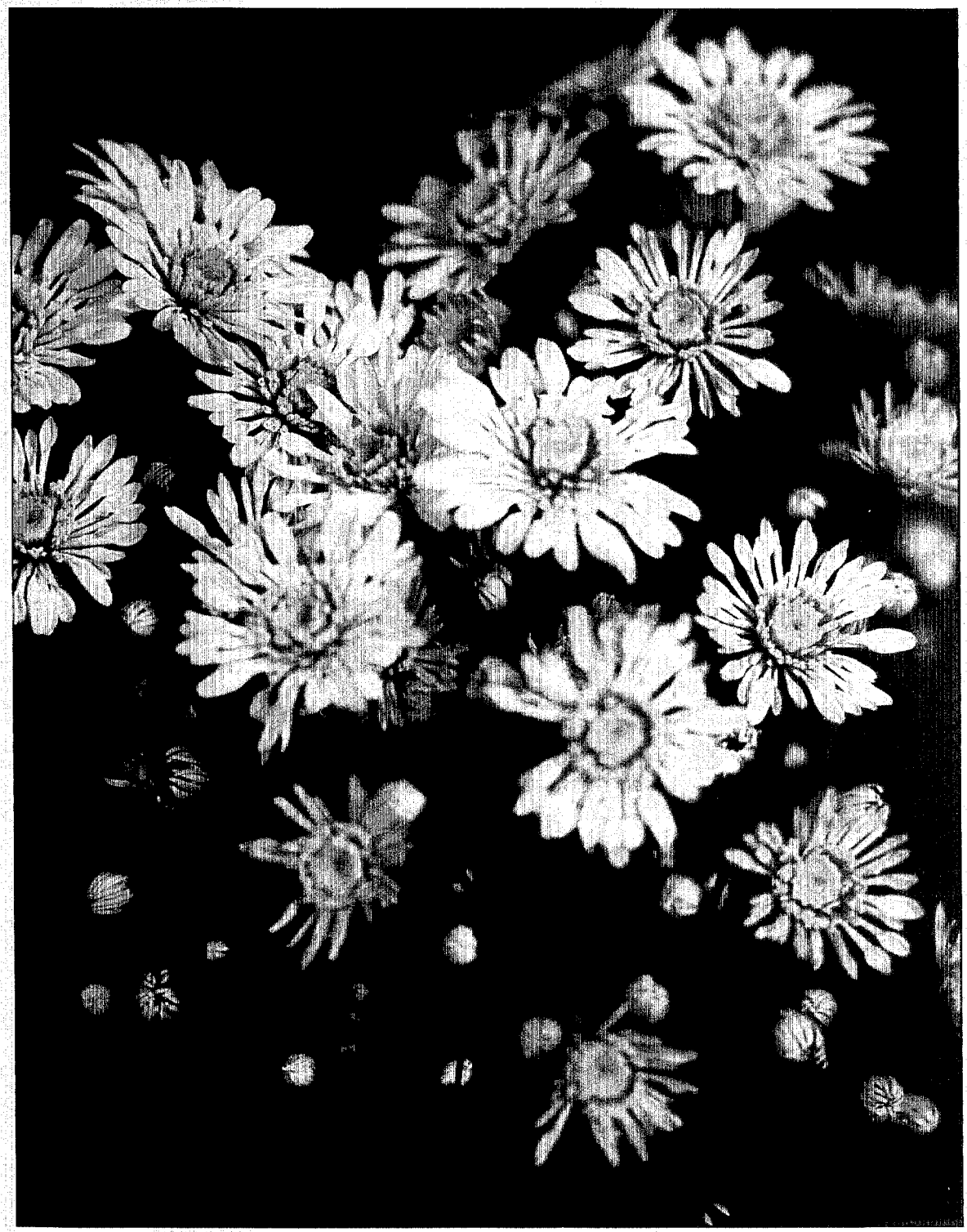

* * * * *